United States Patent [19]

VanMalderen

[11] Patent Number: 4,574,024

[45] Date of Patent: Mar. 4, 1986

[54] APPARATUS AND METHOD OF MANUFACTURING HYGIENIC DISPOSABLE PADS

[75] Inventor: G. P. VanMalderen, Buggenhout, Belgium

[73] Assignee: Ontex PVBA, Buggenhout, Belgium

[21] Appl. No.: 583,891

[22] Filed: Feb. 27, 1984

[51] Int. Cl.⁴ ............................................. B32B 31/10
[52] U.S. Cl. .................................... 156/202; 156/276; 156/291; 156/295; 156/297; 156/464
[58] Field of Search ............... 156/201, 202, 204, 216, 156/291, 276, 279, 297, 289, 248, 295, 249, 300, 301, 552, 461, 464, 522, 269; 604/365, 367, 374, 375, 358, 387, 389, 390; 19/304; 264/112

[56] References Cited

U.S. PATENT DOCUMENTS

| | | | |
|---|---|---|---|
| 3,717,905 | 2/1973 | Furbeck | 19/304 |
| 3,868,287 | 2/1975 | Lewyckyj | 156/202 |
| 4,005,957 | 2/1977 | Savich | 264/112 |
| 4,409,049 | 10/1983 | Passafiume et al. | 156/552 |

*Primary Examiner*—Michael Ball
*Attorney, Agent, or Firm*—Weiser & Stapler

[57] ABSTRACT

Method and apparatus for automatically and continuously forming hygienic disposable pads which includes a fluff forming means and a fluff shaping means. The shaped fluff is passed by a plurality of operation performing stations wherein sheet material is applied to form a package wherein adhesive material is applied to sheet the package and form a functional part of the pad.

9 Claims, 5 Drawing Figures

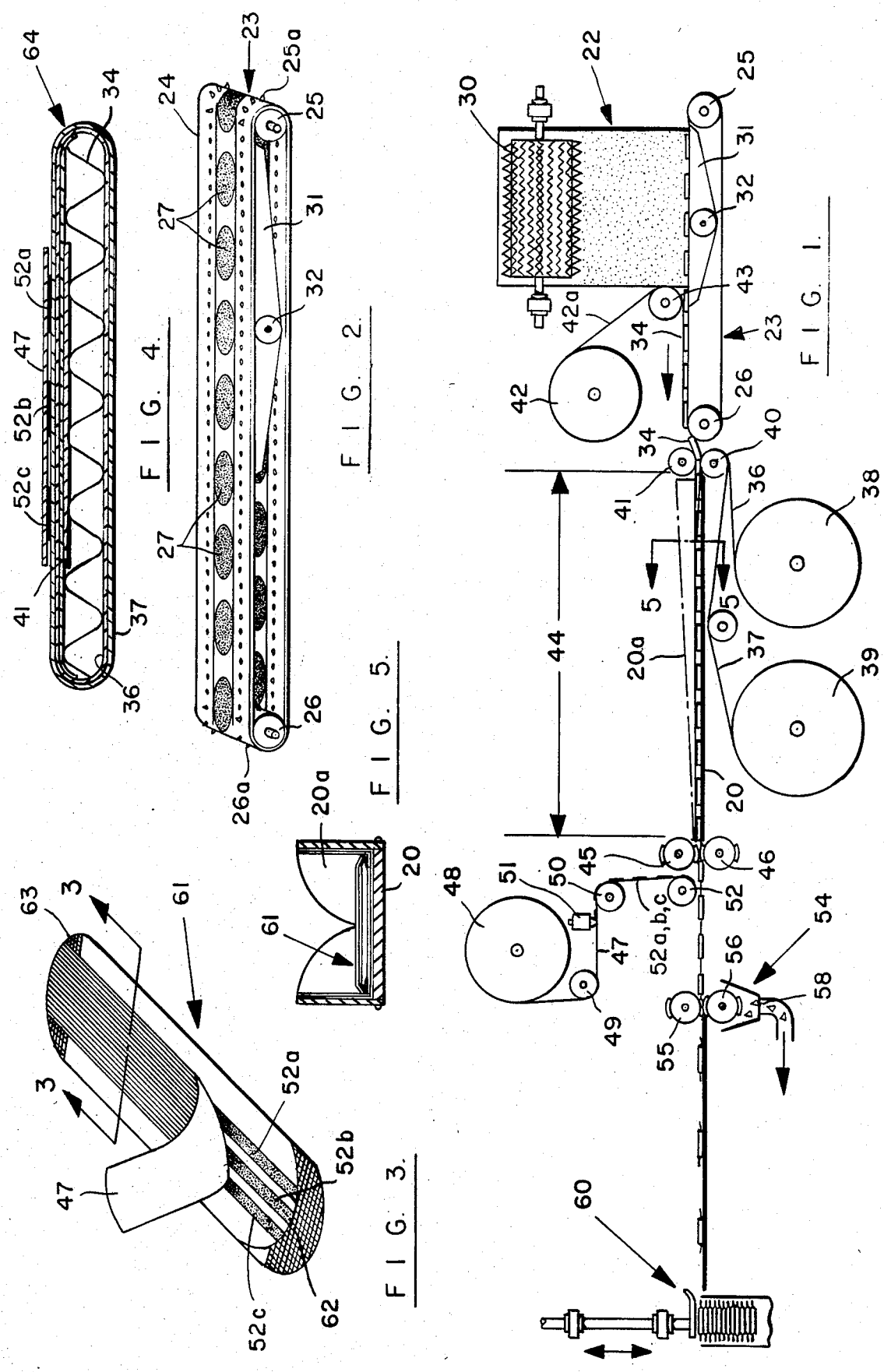

APPARATUS AND METHOD OF MANUFACTURING HYGIENIC DISPOSABLE PADS

The present invention relates to a process and apparatus for preparing catamenial or hygienic disposable pads. More particularly, the invention relates to an apparatus and process for preparing hygienic disposable pads known as "panty shields".

Hygienic disposable pads known as panty shields are usually worn in the crotch of underwear to keep the garment clean. The panty shield is generally made of a super absorbent wadding on a wood pulp base. A thin plastic sheet is placed underneath the super absorbent wadding to prevent humidity from penetrating the garment. This plastic sheet is placed inside the pad to prevent direct skin contact and to avoid skin irritation. Both wadding and plastic sheet are covered by a layer of soft paper tissue which holds them together. An outside layer is utilized which is made of a non-woven fabric having a polyolefin base and containing bonding material. The non-woven fabric is usually permeable to humidity and remains dry itself, so that the skin is never in contact with a wet surface. Both ends of the panty shield are sealed in order to prevent shifting of the wadding. The ends are usually rounded off during manufacture in order to prevent sharp edges from contacting the skin of the user. Adhesive strips are placed on the underside of the pad. Where three adhesive strips are utilized, the middle strip has a double function, namely, sealing the non-woven layer around the pad, and together with the other two strips, keeping the panty shield in the crotch of the undergarment during use.

Generally, in the manufacture of panty shields, there are a series of steps in the manufacture which requires manipulation by supervising personnel.

An important object of the invention is the provision of an apparatus which is adapted to rapidly and automatically manufacture and deliver panty shields in an efficient and effective operation.

Another object of the invention is to provide an improved apparatus or machine in accordance with the foregoing, which is capable of a relatively high production rate, thereby to effect a saving in the time required to manufacture the article.

It is a preferred object of the invention to provide an improved and novel apparatus for manufacturing panty shields wherein there is required a minimum amount of hand labor.

Still another object of the invention is to provide an apparatus having a unique forming and transporting conveyor means which effectively provides the wadding with a definitive shape.

The objectives of the present invention can be achieved by providing an apparatus having forming means for forming fluff into a definitive shape. The forming means is provided with recessed or grooved portions which define the shape of the fluff. Preferably, the recessed or grooved portions are of a mesh material which will permit vacuum forming of the fluff. A fluffer and metering means is associated with the forming means that is capable of grinding paper sheet material into fluff and delivering a minimum amount of the fluff onto the recess of the forming means. Guide means is utilized for effecting continuous travel of the forming means in a predetermined path past the fluffer and metering means. A supply means is associated with the apparatus which supplies three sheets of material that places a double layer on the bottom of the fluff and a single narrower layer on top of the fluff. Powered means may be utilized which effects continuous travel of the shaped fluff from the forming means and the sheets past a plurality of operation-performing stations. Folding means is provided which preferably cooperates with the movement of the powered means and the fluff and strips carried thereon for folding the sides of the two bottom sheet materials onto themselves over the top layer. The apparatus also contains crimping means which crimps the end portions along the ends of the fluff so as to form a package unit. After crimping there are means for applying three strips of adhesive material so that one adhesive strip penetrates the top most layer and seals the package. The adhesive is preferably applied in combination with a protective covering strip. Means are further provided for severing the pad near the end portions so as to form individual package units.

More specifically, it can therefore be seen that the apparatus of the present invention provides for automatically preparing catamenial pads comprising:

A. forming means for forming fluff into a definitive shape with said forming means having portions defining a desired shape;

B. fluffer and metering means associated with the forming means, the fluffer and metering means being capable of grinding sheet material into a fluff and delivering a metered amount of fluff material onto the forming means;

C. drive means for effecting continuous travel of the forming means in a predetermined path past the fluffer and metering means;

D. supply means for supplying three strips of sheet material;

E. guide means for guiding the three strips from the supply means so as to define a double layer on the bottom of the fluff which comprises a tissue layer and a non-woven strip and a layer on the top of the plastic strip material;

F. powered means capable of effecting continuous travel of the shaped fluff past a plurality of operation stations;

G. folding means cooperating with the movement of the powered means, the formed fluff and the three strips carried therewith for folding the sides of the bottom sheets onto the top layer;

H. crimping means for crimping the end portions so as to form a package with the fluff and strips;

I. means for applying adhesive material thereon so as to adhere the portions which are folded on top of the fluff; and J. means for severing the end portions in the crimped portion so as to form individual package units.

Preferably, in accordance with the present invention, the forming means comprises an endless belt having grooves defining a desired shape of the pad or mat. The grooved portions are preferably of mesh material which can be utilized with vacuum means for holding and forming the fluff.

The folding of the tissue and the non-woven sheet is preferably accomplished by folding rails which gradually fold over the outside portions of the bottom layers. However, other conventional folding means may be employed.

Other objects and advantages of the invention will be clear from the following description taken together with the accompanying drawings in which:

FIG. 1 is a diagrammatic view of the apparatus as provided by the invention:

FIG. 2 is a perspective view of the wad forming or shaping means of the apparatus, and FIG. 3 is a perspective view of the article provided by the apparatus.

FIG. 4 is a cross-sectional view of the pad of FIG. 3 along line 3—3.

FIG. 5 is a view along line 5—5 of FIG. 1 showing the sloping walls of the folding rails.

Referring to FIGS. 1 and 2, the apparatus as provided by the invention includes a plurality of sequentially disposed operation-forming stations arranged alongside of an endless conveyor or carrier belt, indicated generally by the numeral 20. Starting at the right-most end of the conveyor, considering FIG. 1, there is located the first step in the production of the pad.

A mat forming zone 22 is provided with a mat forming unit 23 which as shown in FIG. 2 is in the form of an endless belt 24 mounted for rotation around drum 25 and a synchronized drive 26. The conveyor 24 comprises a flexible endless belt having a plurality of spaced mat forming portions 27. Belt 24 is passed around sprockets 25a on drum 25 and sprockets 26a on drive 26. Associated with the belt 24 is a fluffer and metering device 30 in which paper sheet material is ground into tiny fibers and metered onto the forming portions 27. A vacuum or suction 32 is provided at the underside of the belt 24 to further aid in completing the forming of the fluff to the shape of the recess so as to form a shaped mat or wadding 34. As shown in FIG. 1, a vacuum chamber 31 is provided underneath the belt 24 which is connected to a suitable source or means 32 for exhausting air. The mat or wadding 34 is preferably vacuum formed as it continuously travels and traverses the forming station 22.

Upon completion of the mat or wadding forming operation, the mat or wadding 34 is delivered onto a conveyor belt 20 for further processing.

A run of plastic sheet 42a from roll 42 is fed downwardly under a guide roll 43 over the mat coming from the mat forming zone 22 and proceeds to the next work station.

A run of tissue 36 and non-woven sheet material 37 from two rolls 38 and 39 are fed upwardly beneath a pair of guide rolls 40 and 41 simultaneously with the mat 34 and plastic sheet 41. The run of non-woven sheet 37 is preferably of a narrower width than the tissue 36. Supplying of the tissue sheet 36 and non-woven sheet 37 is such that the non-woven sheet 37 forms the base of the arrangement discussed previously.

Immediately after the guide rolls 40 and 41, the components proceed to the folding station 44 in the arrangement shown in FIG. 1. The folding is performed by utilizing gradually sloping sidewalls 20a as shown in FIG. 5 which cause the non-woven sheet 37 and tissue sheet 36 to gradually fold up and over on top of the plastic sheet 42. Immediately after the sheets are folded over, the components are crimped between a pair of crimping rollers 45 and 46 where the portions near the ends of the mat 34 are crimped to form a package. The crimping seals together the tissue and non-woven sheets along the edge of the wadding or mat.

The crimped package then procedes to the next station wherein a run of non-woven slip material, such as silicone coated tape 47, is supplied from a supply drum 48 and guided by means of guide rolls 49 and 50 past an adhesive dispensing unit 51 wherein three adhesive strips 52a, 52b, and 52c are applied. The silicone coated paper is then pressed onto the advancing components by means of compression roller 52 so that the middle adhesive strip 52b penetrates the first layer of the non-woven material and closes the pad package.

The pad then proceeds to a cutting station 54 wherein a pair of cutters 55 and 56 cut in the middle of the sealed portions so that the first half is the end of one pad and the second half is the beginning of the next pad. The edges are rounded to avoid sharp edges. If desired, vacuum means 58 is provided for the removal of the waste cuttings.

The individual pads then proceed to a counting and stacking unit 60 wherein the pads are, preferably, electronically counted and packaged.

In the operation of the apparatus, means is provided for synchronizing the advance of the shaped mat from the mat forming station and the crimping and cutting operation.

One type of pad produced by apparatus of the invention is shown in FIGS. 3 and 4, wherein it will be seen that the pad 61 has an internal wadding 34, a strip of plastic sheet 41 on top of the wadding 34, a tissue 36 forming a thin layer and a non-woven material 37 forming a second layer which is wrapped around the mat 34 and overlies the plastic strip 41. The pad 61 has crimped end portions 62 and 63 which are rounded. Three strips of adhesive material 52a, 52b, and 52c extend from one crimped portion to the other and are covered with a non-stick strip 64, preferably of silicone coated paper, which extends beyond the adhesive portion and to the end of the pad.

It is understood that the apparatus may contain means for synchronizing the various operations at the work stations together with the travel of the sheets and mat from station to station. For example, a power drive may be provided for the conveyor 20 which comprises an electric motor. Conventional means may be provided for removal of the completed pads from the conveyor 20 upon completion of the manufacturing process.

It will be readily understood that the method as provided by the invention embraces the steps of forming a shaped fluff or mat, and moving the mat in a predetermined path past a plurality of operation performing stations which are synchronized so as to provide a continuous manufacturing process. The method of the invention has been shown to be relatively simple and conducive to preparing catamenial pads at a high rate of production. Furthermore, the apparatus has been found to be extremely efficient and effective, and reliable in its operation. It has a high production rate and requires a minimum amount of hand labor. Moreover, the construction of the apparatus does not require costly or intricate special components to be fabricated.

It will be understood that various changes in the details and arrangements of parts which have been herein described and illustrated in order to explain the nature of the invention may be made by those skilled in the art within the principal and scope of the invention.

What is claimed is:

1. Apparatus for automatically and continuously preparing hygienic disposable pads comprising:

A. forming mean for fomeing fluff into a definitive shape, said forming means being a continuous belt with recessed mesh portions defining a desired shape at spaced intervals;
B. fluffer and metering means associated with said forming means, said fluffer and metering means being capable of grinding paper sheet material into fluff and delivering a metered amount of fluff onto said mesh portions of said forming means; said forming means having an associated vacuum source beneath said mesh portions;
C. drive means capable of effecting continuous travel of said forming means in a predetermined path past said fluffer and metering means;
D. supply means for supplying three strips of sheet material;
E. guide means for guiding the strips from said supply means to define a double layer on the bottom of the fluff and one layer on the top;
F. powered means capable of effecting continuous travel of the shaped fluff and strips past a plurality of operation-performing stations;
G. folding means cooperating with the movement of said powered means and the fluff and strips carried thereon for folding the sides of the bottom sheet material onto the top layer;
H. crimping means for crimping the end portions so as to form a package with said fluff and strips;
I. means for simultaneously applying at least three stripes of adhesive material and a protective layer over the folded portion under compression so as to cause one of said adhesive stripes to penetrate the outermost layer and adhere the folded portions and form a closed package; and
J. means for severing the end portions so as to form individual package units.

2. The apparatus of claim 1 wherein said folding means comprises folding rails.

3. The apparatus of claim 1 wherein said fluff and metering means grinds paper material.

4. The apparatus of claim 1 wherein said protective layer is silicone coated tape.

5. The apparatus of claim 1 wherein the three strips of sheet material comprise woven, non-woven, and plastic sheets.

6. The apparatus of claim 1 including means for synchronizing travel of the fluff and operation at each operation performing station.

7. A method for continuously preparing hygienic disposable pads comprising:
A. forming fluff having a definitive shape on a recessed meshed forming means comprising an endless belt having spaced mesh portions;
B. grinding paper sheet material into fluff and delivering a metered amount of fluff onto said forming means while similtaniously passing the mesh portion over a suction source so as to compact said fluff;
C. effecting continuous travel of said forming means in a predetermined path;
D. supplying three strips of sheet material wherein at least one of said strips is non-woven;
E. guiding the strips to define a double layer on the bottom of the shaped fluff wherein said non-woven strip is the outermost layer and one layer on the top;
F. effecting continuous travel of the shaped fluff and strips past a plurality of operation-performing stations;
G. folding the sides of the bottom sheet material onto the top layer;
H. crimping the end portions so as to form a package with said fluff and strips;
I. simultaneously applying at least three stripes of adhesive material and a protective layer over the folded portions under compression so as to cause one of said adhesive stripes to penetrate the outermost layer and adhere the folded portions and form a closed package;
J. severing the end portions so as to form individual package units.

8. The apparatus of claim 7 including effecting a vacuum about said forming means so as to hold and form the fluff.

9. The apparatus of claim 1 including synchronizing travel of the fluff and operation at each operation performing station.

* * * * *